United States Patent [19]
Metzger et al.

[11] 3,954,785
[45] May 4, 1976

[54] ACYLATED UREA COMPOUNDS AND HERBICIDAL COMPOSITIONS

[75] Inventors: Carl Metzger, Dormagen; Ludwig Eue; Wilfried Faust, both of Cologne, all of Germany

[73] Assignee: Bayer Aktiengesellschaft, Leverkusen, Germany

[22] Filed: July 30, 1974

[21] Appl. No.: 493,198

[30] Foreign Application Priority Data
Aug. 10, 1973 Germany............................ 2340570

[52] U.S. Cl............................... 260/306.8 D; 71/90
[51] Int. Cl.².......................................... C07D 285/12
[58] Field of Search............................. 260/306.8 D

[56] References Cited
FOREIGN PATENTS OR APPLICATIONS
1,195,672   6/1970   United Kingdom.......... 260/306.8 D Primary Examiner—R. Gallagher
Assistant Examiner—Mary C. Vaughn
Attorney, Agent, or Firm—Burgess, Dinklage & Sprung

[57] ABSTRACT

New acylated urea compounds of the formula

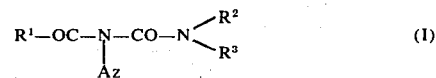

in which
R¹ is alkyl, haloalkyl or optionally substituted aryl,
R² and R³, which may be the same or different, are each alkyl or alkenyl, and
Az is a 1,3,4-thiadiazole radical which is linked in the 2-position and is optionally substituted in the 5-position;

exhibit excellent herbicidal activity and can be used as selective or total herbicides.

16 Claims, No Drawings

ACYLATED UREA COMPOUNDS AND HERBICIDAL COMPOSITIONS

The present invention relates to certain new acylated urea compounds, to herbicidal compositions containing them, and to their use as herbicides.

It is known that 1,1-dimethyl-3-benzoyl-3-(3,4-dichlorophenyl)-urea possesses herbicidal activity and is used as a selective weed-killer in wheat, from French Pat. Nos. 1,250,422 and 1,392,499 and DDR (German Democratic Republic) Patent No. 50,768. However, its activity against some species of weeds, such as species of Galinsoga, Stellaria and Echinochloa, is not always entirely satisfactory, especially if low amounts and low concentrations are used.

The present invention provides, as new compounds, the acylated ureas of the formula

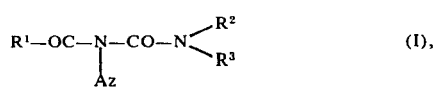

in which
R$^1$ is alkyl, haloalkyl or optionally substituted aryl,
R$^2$ and R$^3$, which may be the same or different, are each alkyl or alkenyl, and
Az is a 1,3,4-thiadiazole radical which is linked in the 2-position and is optionally substituted in the 5-position.

The compounds of the formula (I) have been found to exhibit very good herbicidal properties.

Surprisingly, the acylated ureas according to the invention display a substantially greater herbicidal potency than does the known compound 1,1-dimethyl-3-benzoyl-3-(3,4-dichlorophenyl)-urea. The compounds according to the invention thus represent an enrichment of the art.

Preferably, R$^1$ is straight-chain or branched alkyl of from one to four carbon atoms, halogenoalkyl of one to three carbon atoms and one to three halogen atoms (especially chlorine) or aryl of six to 10 (especially six) carbon atoms, which aryl may optionally carry one or more substituents selected from straight-chain or branched alkyl of one to four (especially one to three) carbon atoms, alkoxy of one to three (especially of one or two) carbon atoms and halogen (especially chlorine, bromine and fluorine); R$^2$ and R$^3$, independently of one another, are each straight-chain or branched alkyl of one to four (especially one to three) carbon atoms or straight-chain or branched alkenyl of two to four (especially three or four) carbon atoms (examples being methyl, ethyl, isopropyl and allyl); and Az is a 1,3,4-thiadiazole radical which is bonded in the 2-position to the nitrogen atom and may be substituted in the 5-position by straight-chain or branched alkyl of two to six carbon atoms (especially of two to four carbon atoms); by halogenoalkyl of 1 to 5 halogen atoms and one or two carbon atoms, or by alkylthio, aralkylthio, alkylsulfonyl, aralkylsulfonyl, alkylsulfoxyl or aralkylsulfoxyl, which radicals have one to four carbon atoms in the alkyl moieties and six to 10 carbon atoms in the aryl moieties.

The following radicals Az may be mentioned by way of example:

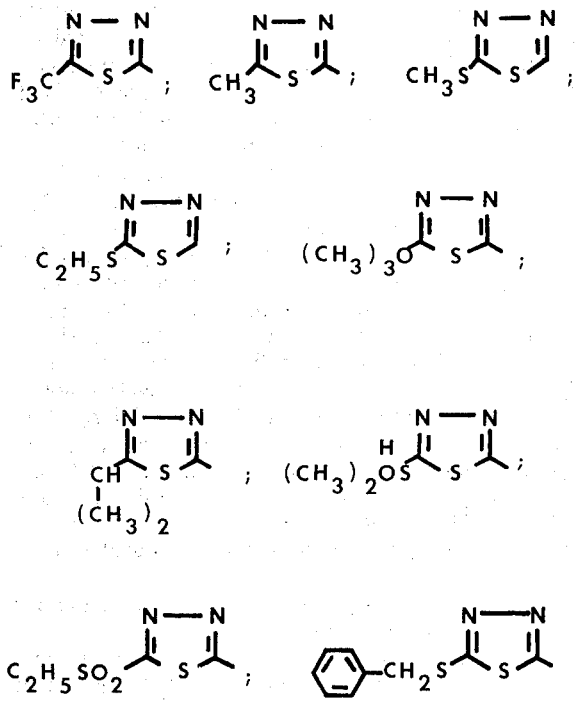

The present invention also provides a process for the preparation of an acylated urea of the formula (I), in which a urea of the formula

in which R$^2$, R$^3$ and Az have the above-mentioned meanings, is reacted with an acid anhydride of the formula

in which R$^1$ has the above-mentioned meaning, optionally in the presence of an inert solvent and a buffer salt.

If 1,1-dimethyl-3-(5-trifluoromethyl-1,3,4-thiadiazol-2-yl)-urea and acetic anhydride are used as starting compounds, the course of the reaction can be represented by the following equation:

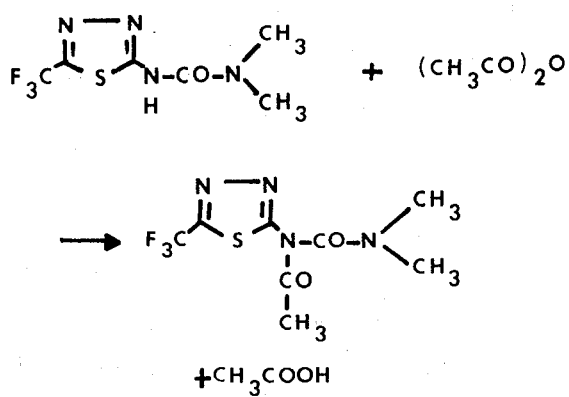

The ureas (II) which can be used according to the invention are already known or can be prepared according to known methods (see German Offenlegungeschriften (German Published Specifications) Pat. Nos. 1,770,467 and 1,670,925, Belgian Pat. No. 743,614 and preparative Example 2 herein).

The following may be mentioned as examples: 1,1-dimethyl-3-(5-n-propyl-thiadiazol-2-yl)-urea, 1,1-dimethyl-3-(5-isopropyl-thiadiazol-2-yl)-urea, 1,1-dimethyl-3-(5-tertiary butyl-thiadiazol-2-yl)-urea, 1,1-dimethyl-3-(5-tertiary-butylthio-thiadiazol-2-yl)-urea, 1,1-dimethyl-3-(5-methylthio-thiadiazol-2-yl)-urea, 1,1-dimethyl-3-(5-methylsulphonyl-thiadiazol-2-yl)-urea, 1,1-dimethyl-3-(5-methylsulphoxyl-thiadiazol-2yl)-urea, 1-methyl-1-ethyl-3-(5-ethylsulphonyl-thiadiazol-2-yl)-urea, 1-methyl-1-allyl-3-(5-butylsulphonyl-thiadiazol-2-yl)-urea, 1,1-dimethyl-3-(5-benzylthio-thiadiazol-2-yl)-urea, 1,1-dimethyl-3-(5-benzylsulphonyl-thiadiazol-2-yl)-urea, 1-methyl-1-isopropyl-3-(5-trifluoromethyl-thiadiazol-2-yl)-urea and 1-methyl-1-isopropyl-3-(5-methylthio-thiadiazol-2-yl)-urea.

The acid anhyrides (III) which can be used according to the invention are known.

All inert solvents can be used as diluents in the process according to the invention. The following may be mentioned as being preferred: hydrocarbons, such as benzene, xylene and toluene, and chlorinated hydrocarbons, such as chlorobenzene and 2,4-dichlorobenzene. However, it is also possible to work without solvents.

The reaction temperatures can be varied within a fairly wide range. In general, the reaction is carried out between 60° and 120°C, preferably between 80° and 100°C.

In carrying out the process according to the invention, about one mole of acid anhydride and about one mole of a buffer salt, for example sodium acetate or, if a solvent is not used, three to four moles of acid anhydride, are generally employed per mole of urea of the formula (II). A further excess above the stoichiometric amount does not produce any improvement in yield worth mentioning.

To isolate the active compounds according to the invention, the solvent or excess anhydride is distilled off, the residue is taken up in an organic solvent, the solution is washed with aqueous alkali until free of the last residue of acid, the organic phase is freed from the solvent and the residue is purified by recrystallization.

The preparation of the compounds of this invention is illustrated in the following preparative Examples.

EXAMPLE 1

Preparation of
1,1-dimethyl-3-acetyl-3-(5-ethylsulfonyl-1,3,4-thiadiazol-2-yl)-urea $$C_2H_5SO_2 \underset{}{\overset{N-N}{\underset{S}{\bigtriangleup}}} \underset{COCH_3}{N-CO-N(CH_3)_2} \quad (1)$$

26.4 g (0.1 mol) of 1,1-dimethyl-3-(5-ethylsulfonyl-1,3,4,-thiadiazol-2-yl)-urea, 41 g (0.4 mol) of acetic anhydride and 1 g of sodium acetate were heated to 100°C for 20 hours. After cooling, the excess acetic anhydride and the acetic acid formed were distilled off, the residue was dissolved in 200 ml of methylene chloride and this solution was shaken with 100 ml of 10 percent strength aqueous sodium hydroxide solution and washed with water until free of alkali. The organic phase was dried over sodium sulfate and freed from the solvent in vacuo.

26.9 g (88% of theory) of 1,1-dimethyl-3-acetyl-3-(5-ethylsulfonyl-1,3,4-thiadiazol-2-yl)-urea of melting point 145°C (ethyl acetate) were obtained.

EXAMPLE 2

Preparation of
1,1-dimethyl-3-acetyl-3-(5-trifluoromethyl-1,3,4-thiadiazol-2-yl)-urea

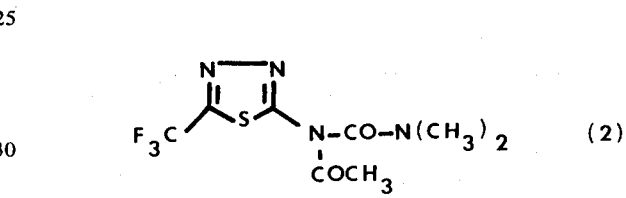

A mixture of 50.5 g (0.21 mol) of 1,1-dimethyl-3-(5-trifluoromethyl-1,3,4-thiadiazol-2-yl)-urea and 100 ml of acetic anhydride was heated, after addition of 1 g of anhydrous sodium acetate, to 100°C for 2 hours. The excess acetic anhydride was distilled off in vacuo and the residue was recrystallized from ligroin/ethyl acetate.

45.1 g (76.5% of theory) of 1,1-dimethyl-3-acetyl-3-(5-trifluoromethyl-1,3,4-thiadiazol-2-yl)-urea of melting point 61°–63°C were obtained.

The starting material was prepared as follows:

$$F_3C \underset{}{\overset{N-N}{\underset{S}{\bigtriangleup}}} \underset{H}{N-CO-N(CH_3)_2}$$

A mixture of 169 g (1 mole) of 5-amino-2-trifluoromethyl-1,3,4-thiadiazole and 101 g (1 mole) of triethylamine in 600 ml of dry tetrahydrofuran was added dropwise to a solution of 156.5 g (1 mole) of chloroformic acid phenyl ester in 1,000 ml of dry tetrahydrofuran at 30°C, whilst stirring and cooling with ice. The mixture was then stirred for 30 minutes at 20°C and thereafter for a further 2 hours, at 40°C. After cooling, the triethylamonium chloride was filtered off and the filtrate is distilled off in vacuo. The residue was recrystallized from ethyl acetate.

228.2 g (79% of theory) of N-(5-trifluoromethyl-1,3,4-thiadiazol-2-yl)-phenylcarbamate of melting point 181°–182°C were obtained.

A mixture of 57.8 g (0.2 mole) of N-(5-trifluoromethyl-1,3,4-thiadiazol-2-yl(-phenylcarbamate and 85 ml of 42.9% strength (0.819 mole) aqueous dimethylamine solution was heated to 70°C for 2 hours, whilst stirring. After cooling, it was poured into 500 ml of water and neutralized with dilute hydrochloric acid whilst cooling with ice, and the precipitate which separated out was filtered off.

After drying, 41.5 g (86.5% of theory) of 1,1-dimethyl-3-5(5-trifluoromethyl-1,3,4-thiadiazol-2-yl)-urea of melting point 152°–153°C (from ligroin) were obtained.

The active compounds listed in Table 1 which follows could be prepared by methods analogous to those described in Examples 1 and 2:

Table 1

$$R^1-OC-N-CO-N{\overset{R^2}{\underset{R^3}{<}}} \quad (I)$$
$$\underset{Az}{|}$$

| Ex. No. | Az | $R^1$ | $R^2$ | $R^3$ | Melting point (°C) |
|---|---|---|---|---|---|
| 3 | 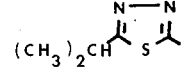 | $CH_3$ | $CH_3$ | $CH_3$ | 55 |
| 4 | 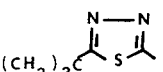 | $CH_3$ | $CH_3$ | $CH_3$ | 68 |
| 5 | 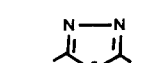 | $CH_3$ | $CH_3$ | $CH_3$ | 95 |
| 6 | 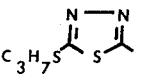 | $CH_3$ | $CH_3$ | $CH_3$ | 46 |
| 7 | 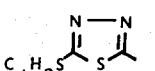 | $CH_3$ | $CH_3$ | $CH_3$ | 63 |
| 8 | 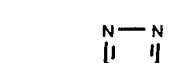 | $CH_3$ | $CH_3$ | $CH_3$ | 63 |
| 9 | 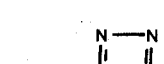 | $CH_3$ | $CH_3$ | $CH_3$ | 110 |
| 10 | 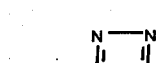 | $CH_3$ | $CH_3$ | $CH_3$ | 108 |

The ureas to be used as starting compounds could be prepared by methods analogous to that given after Example 2; appropriate examples are listed in Table 2 which follows:

Table 2

$$R^4{\overset{N-N}{\underset{S}{\diagdown\diagup}}}NH-CO-N{\overset{R^2}{\underset{R^3}{<}}} \quad (IIa)$$

| Example No. | $R^4$ | $R^2$ | $R^3$ | Melting point (°C) |
|---|---|---|---|---|
| (a) | n-$C_3H_7$ | $CH_3$ | $CH_3$ | 130 |
| (b) | $CH(CH_3)_2$ | $CH_3$ | $CH_3$ | 126 |
| (c) | $C(CH_3)_3$ | $CH_3$ | $CH_3$ | 132 |
| (d) | $CH_3S$ | $CH_3$ | $CH_3$ | 189 |
| (e) | $CH_3SO_2$ | $CH_3$ | $CH_3$ | 195 |
| (f) | $C_2H_5S$ | $CH_3$ | $CH_3$ | 106 |
| (g) | $C_2H_5SO_2$ | $CH_3$ | $CH_3$ | 161 |
| (h) | n-$C_3H_7S$ | $CH_3$ | $CH_3$ | 129 |
| (i) | n-$C_3H_7SO_2$ | $CH_3$ | $CH_3$ | 167 |
| (j) | $SCH(CH_3)_2$ | $CH_3$ | $CH_3$ | 138 |
| (k) | $SO_2CH(CH_3)_2$ | $CH_3$ | $CH_3$ | 195 |

Table 2-continued $$R^4 \underset{\substack{\| \quad \|\\S}}{\overset{N-N}{\diagup \diagdown}} NH-CO-N \diagup \overset{R^2}{\diagdown R^3} \quad (IIa)$$

| Example No. | R⁴ | R² | R³ | Melting point (°C) |
|---|---|---|---|---|
| (l) | n-C₄H₉S | CH₃ | CH₃ | 131 |
| (m) | n-C₄H₉SO₂ | CH₃ | CH₃ | 168 |
| (n) | SCH—C₂H₅<br>\|<br>CH₃ | CH₃ | CH₃ | 80 |
| (o) | SO₂CH—C₂H₅<br>\|<br>CH₃ | CH₃ | CH₃ | 172–173 |
| (p) | SC(CH₃)₃ | CH₃ | CH₃ | 153 |
| (q) | SO₂C(CH₃)₃ | CH₃ | CH₃ | 239 |

The active compounds according to the invention display a strong herbicidal activity and can therefore be used for combating weeds.

Weeds, in the broadest sense, are plants which grow in locations where they are not desired. As weeds there may be mentioned: dicotyledons such as mustard (Sinapis), cress (Lepidium), cleavers (Galium), chickweed (Stellaria), camomile (Matricaria), gallant soldier (Galinsoga), goosefoot (Chenopodium), annual nettle (Urtica) and groundsel (Senecio) and monocotyledons such as timothy (Phleum) bluegrass (Poa), fescue (Festuca), goosegrass (Eleusine), foxtail (Setaria), ryegrass (Lolium) and barnyard grass (Echinochloa).

The active compounds according to the invention have a very strong influence on plant growth, but in different ways, so that they can be used as selective herbicides, defoliants and desiccants. They show particular advantages as selective herbicides in cultures of cotton, maize, and cereals. At higher concentrations they can also be employed as total herbicides.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

The active compounds according to the invention can be present in the formulations as a mixture with other active compounds.

The formulations in general contain from 0.1 to 95 percent by weight of active compound, preferably from 0.5 to 90 percent by weight.

The active compounds can be used as such, in the form of their formulations or as the use forms prepared therefrom, such as ready-to-use solutions, emulsions, powders, pastes and granules. They may be used in the customary manner, for example by watering, spraying, atomising, scattering and dusting.

They can be used either by the post-emergence process or by the pre-emergence process; they are preferably used after the emergence of the plants.

The amount of active compound employed can vary within fairly wide ranges; it depends essentially on the nature of the desired effect. In general, the amounts used are between 0.1 and 20 kg/ha, preferably between 0.5 and 8 kg/ha.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds or a weed habitat a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier. It will be seen that the usual methods of providing a harvested crop may be improved by the present invention.

The herbicidal activity of the compounds of this invention is illustrated by the following biotest Examples.

EXAMPLE A

Post-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants, which had a height of 5–15 cm, were sprayed with the preparation of the active compound in such a way as to apply the amounts of active compound per unit area which are indicated in the table. The amount of water used was 2,000 l/ha. After three weeks, the degree of damage to the plants was determined and characterized by the values 0 – 5, which have the following meaning:

0 no effect
1 a few slightly burnt spots
2 marked damage to leaves
3 some leaves and parts of stalks partially dead
4 plant partially destroyed
5 plant completely dead.

The active compounds, the amounts used and the results can be seen from the table which follows:

To produce a suitable preparation of active compound, 1 part by weight of active compound was mixed with the stated amount of solvent, the stated amount of emulsifier was added and the concentrate was then diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants was determined and characterized by the values 0–5, which have the following meaning:

0 no effect

Table A

| Active compound | Amount of active compound used, kg/ha | Echinochloa | Chenopodium | Sinapis | Galinsoga | Stellaria | Urtica | Matricaria | Daucus | Oats | Cotton | Wheat |
|---|---|---|---|---|---|---|---|---|---|---|---|---|
| $C_2H_5SO_2$—[thiadiazole]—N(COCH$_3$)—CO—N(CH$_3)_2$ (1) | 2<br>1 | 5<br>5 | 5<br>5 | 5<br>5 | 5<br>5 | 5<br>5 | 5<br>5 | 5<br>4 | 5<br>5 | 4–5<br>4–5 | 4<br>3 | 4–5<br>4–5 |
| $C_3H_7SO_2$—[thiadiazole]—N(COCH$_3$)—CO—N(CH$_3)_2$ (9) | 2<br>1 | 5<br>5 | 5<br>4–5 | 5<br>5 | 3<br>1 | 5<br>5 | 5<br>5 | 5<br>3 | 5<br>4 | 4<br>3 | 2<br>0 | 1<br>0 |
| 2,3-dichlorophenyl–C(O)–N–C(O)–N(CH$_3)_2$ (known) | 2<br>1 | 1<br>1 | 3<br>1 | 4–5<br>4 | 2<br>1 | 5<br>3 | 2<br>2 | 1<br>0 | 1<br>0 | 1<br>0 | 0<br>0 | 0<br>0 |

EXAMPLE B

Pre-emergence test

Solvent: 5 parts by weight of acetone
Emulsifier: 1 part by weight of alkylaryl polyglycol ether.

1 slight damage or delay in growth
2 marked damage or inhibition of growth
3 heavy damage and only deficient development or only 50% emerged
4 plants partially destroyed after germination or only 25% emerged
5 plants completely dead or not emerged.

The active compounds, the amounts applied and the results obtained can be seen from the following table:

Table B

| Active compound | Amount of active compound used, kg/ha | Sinapis | Echinochloa | Chenopodium | Lolium | Stellaria | Galinsoga | Matricaria | Oats | Cotton | Wheat | Maize |
|---|---|---|---|---|---|---|---|---|---|---|---|---|
| $C_2H_5SO_2$—[thiadiazole]—N(COCH$_3$)—CO—N(CH$_3)_2$ (1) | 2.5<br>1.25 | 4–5<br>3 | 5<br>5 | 5<br>5 | 4–5<br>4–5 | —<br>— | 5<br>4 | 5<br>5 | 1<br>0 | 1<br>0 | 1<br>0 | 3<br>2 |

Table B-continued

| | | Pre-emergence test | | | | | | | | | | |
|---|---|---|---|---|---|---|---|---|---|---|---|---|
| Active compound | Amount of active compound used, kg/ha | Sinapis | Echinochloa | Chenopodium | Lolium | Stellaria | Galinsoga | Matricaria | Oats | Cotton | Wheat | Maize |
| C₃H₇SO₂—[thiadiazole]—N(CO-N(CH₃)₂)(COCH₃) (9) | 2.5<br>1.25 | 4–5<br>3 | 5<br>4–5 | 5<br>4–5 | 5<br>5 | 5<br>5 | 3<br>3 | 5<br>5 | 1<br>0 | 4<br>3 | 3<br>2 | 1<br>0 |
| (2,3-dichlorophenyl)-C(O)-N-C(O)-N(CH₃)₂ (known) | 2.5<br>1.25 | 3<br>3 | 2<br>1 | 3<br>2 | 2<br>2 | 4–5<br>4–5 | 2<br>2 | 4<br>4 | 0<br>0 | 2<br>2 | 0<br>0 | 2<br>2 |

It will be understood that the foregoing specification and examples are illustrative but not limitative of the present invention inasmuch as other embodiments within the spirit and scope of the invention will suggest themselves to those skilled in the art.

What is claimed is:

1. Acylated urea compound of the formula:

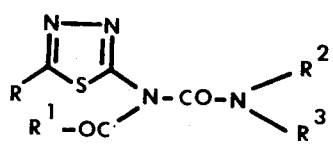

wherein
$R^1$ is methyl;
$R^2$ and $R^3$ are individually selected from alkyl and alkenyl of up to four carbon atoms; and
R is alkyl of from two to six carbon atoms, benzylthio, benzylsulfonyl, benzylsulfoxyl, alkylthio, alkylsulfonyl, alkylsulfoxyl or haloalkyl, wherein the alkyl moieties contain from one to four carbon atoms.

2. Acylated urea compound as claimed in claim 1 wherein $R^2$ is alkyl.

3. Acylated urea compound as claimed in claim 1 wherein $R^2$ is alkenyl.

4. Acylated urea compound as claimed in claim 1 wherein $R^3$ is alkyl.

5. Acylated urea compound as claimed in claim 1 wherein $R^3$ is alkenyl.

6. Acylated urea compound as claimed in claim 1 wherein one of $R^2$ and $R^3$ is alkyl and the other is alkenyl.

7. Acylated urea compound as claimed in claim 1 wherein both of $R^2$ and $R^3$ are alkyl.

8. Acylated urea compound as claimed in claim 1 wherein both of $R^2$ and $R^3$ are alkenyl.

9. Acylated urea compound as claimed in claim 1 wherein R is alkyl.

10. Acylated urea compound as claimed in claim 1 wherein R is benzylthio, benzylsulfonyl or benzylsulfoxy.

11. Acylated urea compound as claimed in claim 1 designated 1,1-dimethyl-3-acetyl-3-(5-ethylsulfonyl-1,3,4-thiadiazol-2-yl)-urea.

12. Acylated urea compound as claimed in claim 1 designated 1,1-dimethyl-3-acetyl-3-(5-trifluoromethyl-1,3,4-thiadiazol-2-yl)-urea.

13. Acylated urea compound as claimed in claim 1 designated 1,1-dimethyl-3-acetyl-3-(5-n-propylsulfonyl-1,3,4-thiadiazol-2-yl)-urea.

14. Acylated urea compound as claimed in claim 1 designated 1,1-dimethyl-3-acetyl-3-(5-n-butylsulfonyl-1,3,4-thiadiazol-2-urea.

15. Acylated urea compound as claimed in claim 1 wherein R is alkylthio, alkylsulfonyl or alkylsulfoxy.

16. Acylated urea compound as claimed in claim 1 wherein R is haloalkyl.

* * * * *